United States Patent
Bruder et al.

(10) Patent No.: US 7,302,030 B2
(45) Date of Patent: Nov. 27, 2007

(54) METHOD FOR DETERMINATION OF THE POSITION AND/OR ORIENTATION OF THREE-DIMENSIONAL STRUCTURES OF A PATIENT WITH THE AID OF A COMPUTED TOMOGRAPHY SCANNER

(75) Inventors: Herbert Bruder, Hoechstadt/Aisch (DE); Sven Skaberna, Wiesenthau (DE)

(73) Assignee: Siemens Aktiengesellschaft, Munich (DE)

( * ) Notice: Subject to any disclaimer, the term of this patent is extended or adjusted under 35 U.S.C. 154(b) by 178 days.

(21) Appl. No.: 11/038,138

(22) Filed: Jan. 21, 2005

(65) Prior Publication Data

US 2006/0013356 A1    Jan. 19, 2006

(30) Foreign Application Priority Data

Jan. 23, 2004   (DE) .................. 10 2004 003 532

(51) Int. Cl.
*G01N 23/00* (2006.01)
(52) U.S. Cl. ............................................. 378/9; 378/4
(58) Field of Classification Search .................. 378/4, 378/9, 11, 20
See application file for complete search history.

(56) References Cited

U.S. PATENT DOCUMENTS

| | | | |
|---|---|---|---|
| 4,174,481 A | 11/1979 | Liebetruth | |
| 4,196,352 A | 4/1980 | Berninger et al. | |
| 4,477,922 A | 10/1984 | Liebetruth | |
| 4,570,263 A | 2/1986 | Liebetruth | |
| 4,570,264 A | 2/1986 | Liebetruth | |
| 4,868,843 A * | 9/1989 | Nunan | 378/152 |
| 4,991,190 A | 2/1991 | Mori | |
| 5,068,882 A * | 11/1991 | Eberhard | 378/4 |
| 5,247,556 A | 9/1993 | Eckert et al. | |
| 5,450,462 A | 9/1995 | Toth et al. | |
| 6,067,341 A * | 5/2000 | Horiuchi | 378/8 |
| 6,198,790 B1 * | 3/2001 | Pflaum | 378/9 |
| 6,385,280 B1 | 5/2002 | Bittl et al. | |
| 6,421,412 B1 | 7/2002 | Hsieh et al. | |
| 6,512,808 B2 | 1/2003 | Klingenbeck-Regn | |
| 2004/0114710 A1 * | 6/2004 | Ozaki | 378/9 |

FOREIGN PATENT DOCUMENTS

| | | |
|---|---|---|
| DE | 26 13 809 | 10/1977 |
| DE | 41 03 588 C1 | 5/1992 |
| DE | 195 32 535 A1 | 3/1996 |
| DE | 198 02 405 A1 | 8/1999 |
| DE | 199 61 524 A1 | 12/1999 |
| DE | 199 33 537 A1 | 5/2000 |
| DE | 103 02 565 A1 | 8/2004 |
| EP | 1 062 911 A2 | 12/2000 |
| EP | 1 304 077 A2 | 4/2003 |

* cited by examiner

*Primary Examiner*—Hoon Song
(74) *Attorney, Agent, or Firm*—Harness, Dickey & Pierce, P.L.C.

(57) ABSTRACT

A method is for determination of at least one of the position and orientation of three-dimensional structures of a patient. One topographic scan of the patient is recorded simultaneously per tube detector combination with the aid of a computed tomography scanner which has at least two tube detector combinations arranged at a fixed angle to one another. Each detector has at least one row with a large number of individual detector elements. The at least two tube detector combinations are moved exclusively linearly parallel to the system axis of the CT and relative to the patient.

33 Claims, 5 Drawing Sheets

METHOD FOR DETERMINATION OF THE POSITION AND/OR ORIENTATION OF THREE-DIMENSIONAL STRUCTURES OF A PATIENT WITH THE AID OF A COMPUTED TOMOGRAPHY SCANNER

The present application hereby claims priority under 35 U.S.C. §119 on German patent application numbers DE 10 2004 003 532.6 filed Jan. 23, 2004, the entire contents of which is hereby incorporated herein by reference.

FIELD OF THE INVENTION

The invention generally relates to a method for determination of the position and/or orientation of three-dimensional structures of a patient using a computed tomography scanner; preferably by recording topographic scans at an angle to one another.

BACKGROUND OF THE INVENTION

Fundamentally, the recording of topographic scans with the aid of computed tomography scanners has been known for a long time. For example, published Specification DE 26 13 809 describes a method for production of transverse layer images with the aid of a tube detector unit, with the detector having a large number of individual detectors and the tube detector combination being shifted with a linear movement relative to the patient in order to produce the transverse layer images, and with a transverse layer image or else topographic scan being obtained from the measured data obtained during the relative movement of the tube detector combination with respect to the patient.

Patent Specification DE 41 03 588 C1 describes a computed tomography scanner which has a rotating tube detector combination which on the one hand rotates about the central axis, and is at the same time shifted relative to the patient in the direction of the central axis. This is done in order to scan a patient. The scanning data from specific projection directions is used in order once again to create a topographic scan by composition of the measured data from these specific projection directions. The radiation load on the patient is, of course, relatively high during a measurement such as this since the patient is also subjected to a dosage load at projection angles which are not required for the topographic scan.

Laid-Open Specification DE 199 61 524 A1 also discloses a scanning method such as this with a computed tomography scanner for a patient. A topographic scan is also determined in this case during a spiral scan by adding up the measured data at the detector system for specific projection angles from the measured data determined during the spiral scan so that this data is combined to form a topographic scan or X-ray shadow image. This is done in order to make it possible to use this to determine the position and/or orientation of specific areas which are intended to be examined in more detail.

Furthermore, Laid-Open Specification DE 198 02 405 A1 also discloses a combination of a CT with a tube matrix detector combination and with an X-ray having a tube solid-state image converter combination. These are arranged at an angle of 90° to one another on a rotating rim. This appliance produces CT section images and X-ray shadow images at the same time, with the total dose that is applied in this case also being relatively high. Furthermore, only shadow images on one plane can be created in one operation.

While only topographic scans are produced in each of the documents cited above, in order to determine the position and/or orientation of regions of interest on a plane, the Laid-Open Specification DE 195 32 535 A1 mentions that the three-dimensional position and/or orientation of structures of interest can also be obtained by producing two orthogonal views or topographic scans. In order to produce these two topographic scans at an angle to one another as required for this purpose, a single-tube computed tomography scanner is used which either produces the two topographic scans that are required by linear scanning twice from different projection angles, or the measured values during a spiral scan are added up at at least two projection angles, thus resulting in the appropriate topographic scans.

The knowledge of the three-dimensional structure, for example the position, orientation and extent of the patient or the knowledge of the position, orientation and extent of a tumor in a patient is used either for dosage modulation for a subsequent CT scan or for radiation therapy planning in a radiation therapy appliance. With regard to dosage modulation, reference should be made, for example, to Laid-Open Specification DE 199 33 537 A1 or to the already cited Laid-Open Specification DE 195 32 535 A1.

SUMMARY OF THE INVENTION

An object of an embodiment of the invention is to find a method for determination of the position and/or orientation of three-dimensional structures of a patient with the aid of a computed tomography scanner. In particular, the method can be one which can be carried out quickly and with little dosage load.

The inventors have found, in one embodiment, that the use of a computed tomography scanner with at least two tubes arranged at offset angles can be used particularly advantageously for fast and simultaneous production of topographic scans of a patient in order in this way to determine the three-dimensional structure of a patient while the dosage load is at the same time low. This relates, of course, only to the determination of a coarse structure, since a method such as this may be less accurate and informative than a complete CT scan. However, two or three topographic scans at an angle to one another make it possible to determine, or at least verify, the position and/or orientation of a three-dimensional structure, for example the position and/or orientation of an organ or of a tumor, sufficiently accurately.

On the basis of this fundamental idea, the inventors propose a method of one embodiment, for determination of the position and/or orientation of three-dimensional structures of a patient, wherein in each case one topographic scan of the patient is recorded simultaneously per tube detector combination with the aid of a computed tomography scanner which has at least two tube detector combinations, which are arranged at a fixed angle to one another and each detector has at least one row with a large number of individual detector elements, with the at least two tube detector combinations being moved exclusively linearly parallel to the system axis of the CT and relative to the patient.

A multi-tube CT, which is known per se, may be used for this method according to an embodiment of the invention. One such CT is disclosed, for example, in U.S. Pat. No. 6,421,412 B1, U.S. Pat. No. 4,991,190 or U.S. Pat. No. 4,196,352. However, a topographic scan such as this is not recorded by passing the tube detector combinations in a complete spiral around the patient. Instead of this, the tube detector combinations are moved linearly along the patient, so that the total applied dose is considerably less than the dose applied during a CT scan. One advantageous feature in this case is that a scan such as this for a topographic scan may be carried out very quickly, and the topographic scans may be recorded simultaneously from the selected projection directions.

At least two topographic scans with a fixed angle between them must be recorded for the method according to an embodiment of the invention. A two-tube detector combination may be used for this purpose, in which case the two tubes should preferably be arranged at right angles to one another. However, in principle, it is sufficient for position and/or orientation determination to record two topographic scans with tubes which are arranged at any desired angle, with the exception of 0° or 180°, with respect to one another, although the precision of the position determination process is decreased as the angle offset approaches 0° or 180°. It is also possible for the X-ray tubes to be offset in the direction of the system axis, but this offset must be taken into account during the subsequent evaluation of the topographic scans.

One feature of an embodiment of the invention is the fixed angle between the two tubes, which as far as possible should preferably be fixed mechanically since this is a way to ensure that the geometric association is sufficiently accurate. If, in contrast to this, a single-tube system is used, with two scans offset through a specific angle, then this results in considerably greater inaccuracy in the localization. This is because, on the one hand, the angle cannot be set with the same precision, and on the other hand because movement in the object between the two scans can lead to inaccuracies.

However, in addition to the simultaneous recording of two topographic scans, it is also possible to use a three-tube detector combination. As such, three topographic scans are recorded at the same time during one scan, with the three-tube detector combinations preferably being at a fixed angle of 120° with respect to one another. This also results in the planes for the topographic scans intersecting at 120°.

In the same way as for the prior art cited above, tube detector combinations are suitable for use in an embodiment of this method which, for example, each have their own detector, which covers exclusively one beam fan of a tube. However, it is also possible to use tube detector combinations which on the one hand have two or more tubes and on the other hand have a single common detector, which is in the form of a circular arc and covers 360°. Each tube may produce a beam fan which does not overlap the other beam fan or fans of the other tubes.

Furthermore, the inventors propose that, when using curved detectors the topographic scan recorded by these detectors can be converted to the geometric data of a virtual, planar detector.

Fundamentally, a wide range of different geometric analysis procedures can be used to determine the position and/or orientation of individual structures from the topographic scans. For example, the volume of the projection fans between the beam focus and the image can be calculated from the boundaries of the object in a recorded topographic scan in order to determine the three-dimensional extent, position and/or orientation of an object, with the section volume of the calculated projection fan volumes being formed in order to determine the position, orientation and/or contours. Such determination of the three-dimensional extent of an object under consideration admittedly does not result in determination of the fine structure of this object. However, it is sufficient for determination of a coarse structure and for position and/or orientation definition. For example, such determination of the three-dimensional extent of an object may be sufficient to provide the required information for radiation therapy planning, in which case it is particularly advantageous that this information can be obtained with a relatively low radiation dose during the scan to produce the topographic scans, since the radiation dose during radiation therapy is very high in any case so that largely unnecessary additional radiation doses should be avoided.

In accordance with the method according to an embodiment of the invention, the method may, however, be used not only for dosage planning for radiation therapy but also for dosage modulation during a CT scan, thus allowing predictive dosage modulation.

Furthermore, the position of organs, tumors or other structures in the patient can also be determined indirectly by way of markers which are applied to the patient at predetermined positions and can be identified particularly clearly in the topographic scan. If the relative position and orientation of the markers on the patient are known, then, by way of example, it is possible to deduce the position and orientation of a tumor from the position of the markers, which can be identified particularly easily. This indirect position and orientation determination can be used in a particularly helpful manner for the positioning of a patient for radiation therapy.

BRIEF DESCRIPTION OF THE DRAWINGS

The invention will be described in more detail in the following text using exemplary embodiments and with the aid of the figures, in which the following reference symbols are used. 1: first X-ray tube, 2: first beam, 3: first detector, 4: second X-ray tube, 5: second beam, 6: second detector, 7: patient, 8: tumor or organ, 9: frontal topographic scan, 10: lateral topographic scan, 11: system axis/z axis, a: angular offset between the X-ray tubes.

In detail, in the figures.

DETAILED DESCRIPTION OF THE EXEMPLARY EMBODIMENTS

Figure 1:
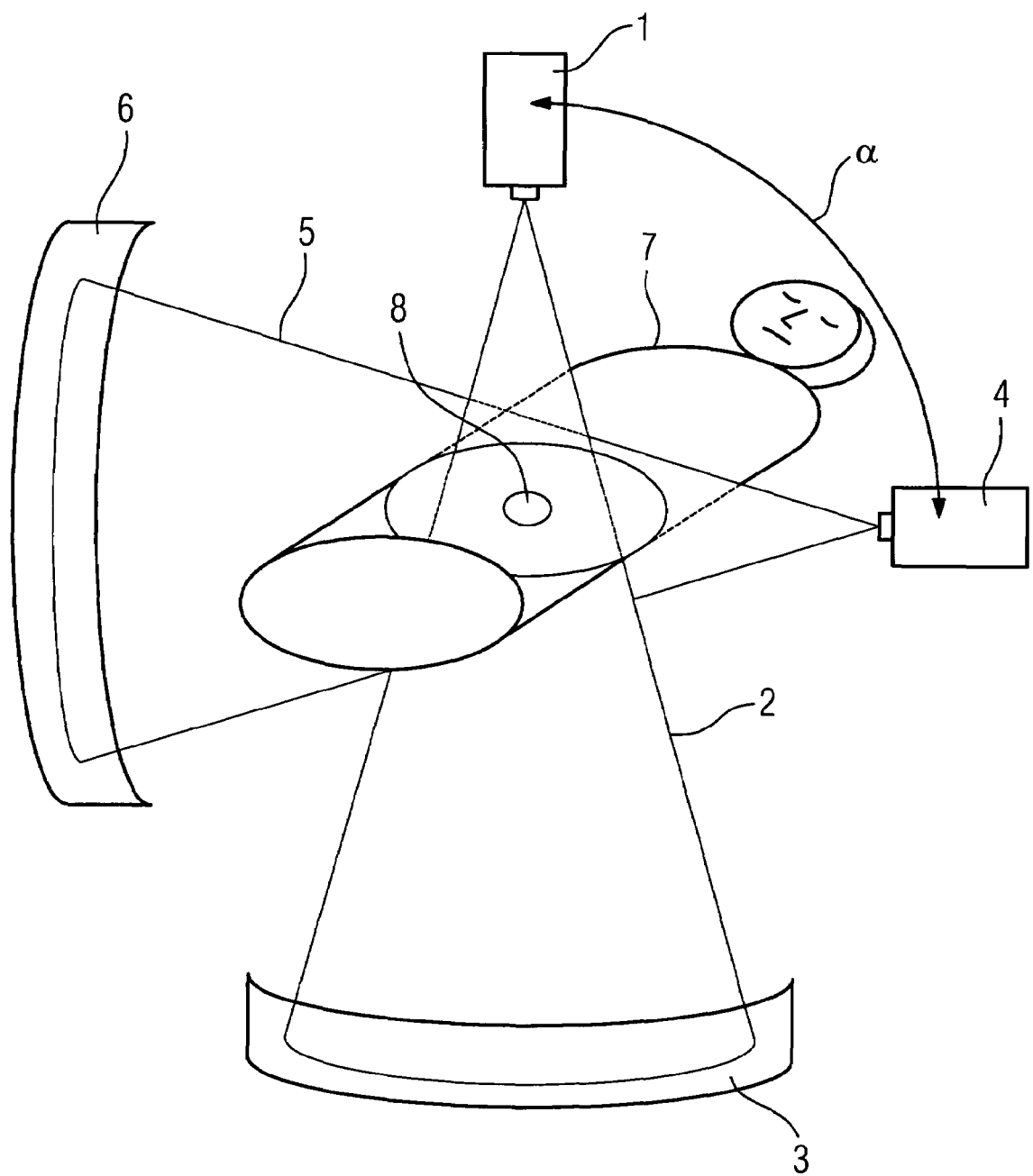
FIG. 1 shows a schematic illustration of a CT scan of a patient, with two tubes offset at right angles to one another.

FIG. 1 shows a stylized patient 7 who is being subjected to a scan for simultaneous recording of two topographic scans with the aid of two X-ray tubes 1 and 4 which are arranged at a fixed angle α to one another and are mechanically coupled. For this purpose, the two X-ray tubes 1 and 4 are moved simultaneously in the direction of the z axis, with the respective beams 2 and 5 that emerge from the X-ray tubes 1 and 4 passing through the patient 7 and being detected on the side opposite the X-ray tubes after they have passed through the patient 7, by detectors 3 and 6 with a large number of small detector elements.

Figure 2:
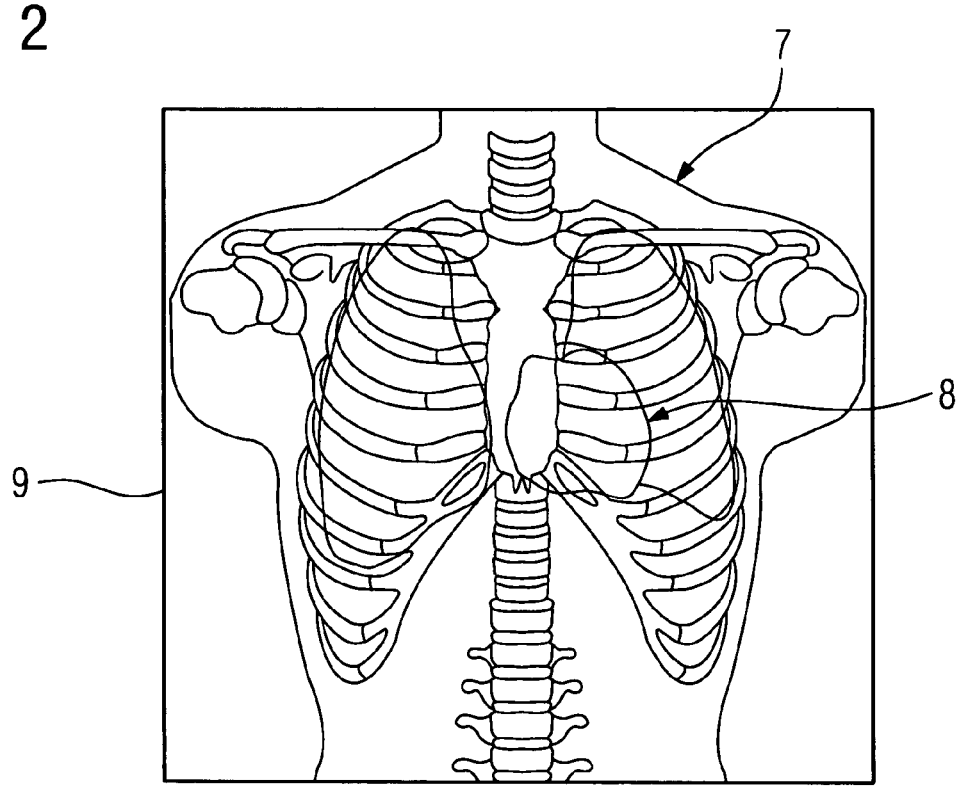
FIG. 2 shows a topographic scan from the first tube.
Figure 3:
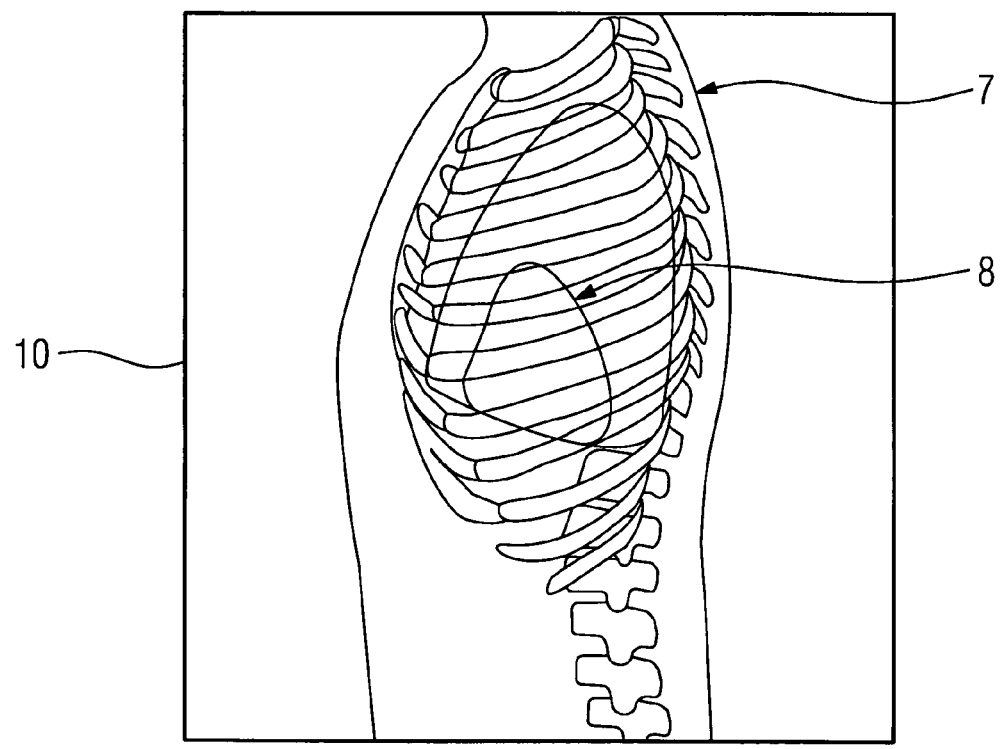
FIG. 3 shows a topographic scan from the second tube.

An image of the radiation attenuation and thus a two-dimensional representation of the patient and of his organs together with any tumors or bones that may be present can thus be generated by each detector by recording the measured radiation intensity as a function of the z position, as is illustrated in FIGS. 2 and 3.

Since the topographic scans are on two mutually independent planes, the three-dimensional position and/or orientation of desired organs or tumors that are illustrated in the topographic scans, for example of the organ 8 that is illustrated schematically in FIG. 1, can now be calculated by simple geometric observations, and can be determined, for example for subsequent radiation therapy or else for a CT scan.

FIGS. 2 and 3 show two such topographic scans 9 and 10, which can respectively be associated with the X-ray tubes 1 and 4 and the detectors 3 and 6. The topographic scan 9 thus represents a frontal scan, and the topographic scan 10 a lateral scan. These topographic scans clearly show, by way of example, the position, orientation and extent of the heart 8 of the patient 7—in this case two-dimensionally—that are intended to be determined.

Figure 4:
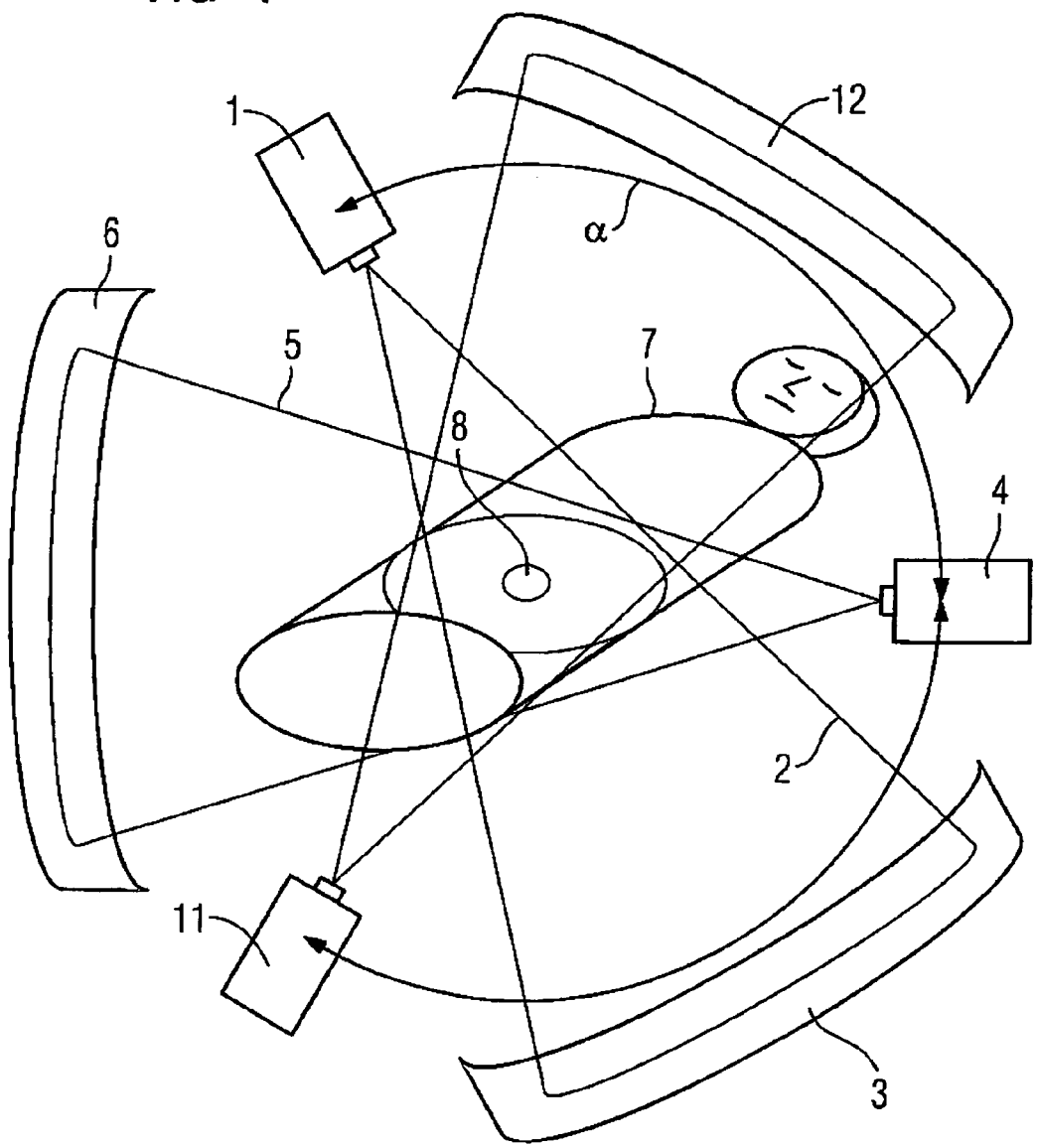
FIG. 4 illustrates an example embodiment including three detector tube combinations.

FIG. 4 illustrates an example embodiment including three detector tube combinations. As shown, each tube 1, 4, and 11 may have a corresponding detector 3, 6, and 12, respectively. The three tube detector combinations are arranged at an angle of 120° to one another. In this example, three topographic scans are recorded with the three tube detector combinations simultaneously.

Figure 5:
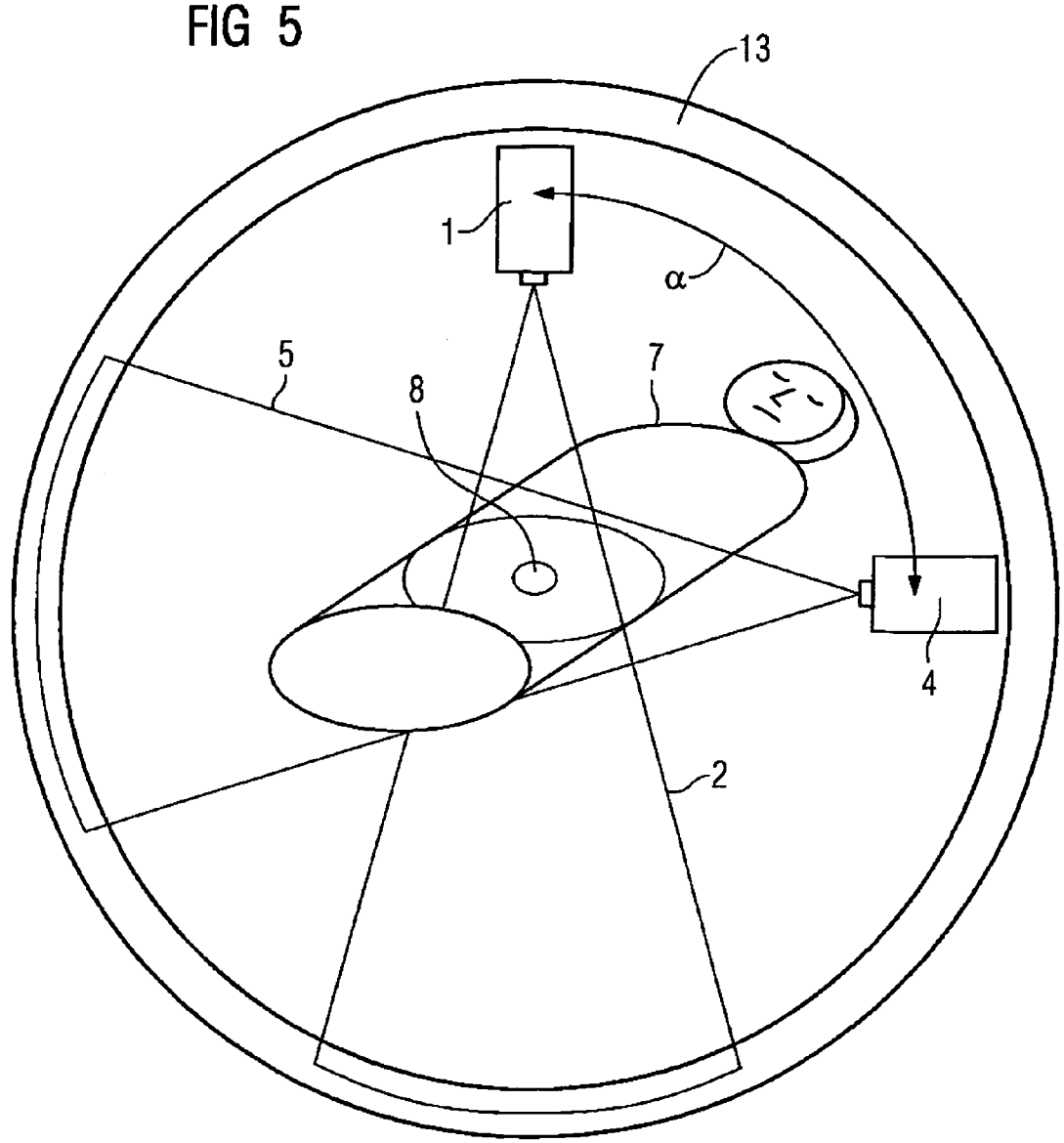
FIG. 5 illustrates an example embodiment including two tubes and a single detector.

FIG. 5 illustrates an example embodiment including two tubes 1, 4 and a single detector 13. This tube detector combination, which on the one hand have two or more tubes or a single common detector, is in the form of a circular arc and covers 360°. Each tube 1, 4 may produce a beam fan 2, 5 which does not overlap the other beam fan or fans of the other tubes.

Figure 6:
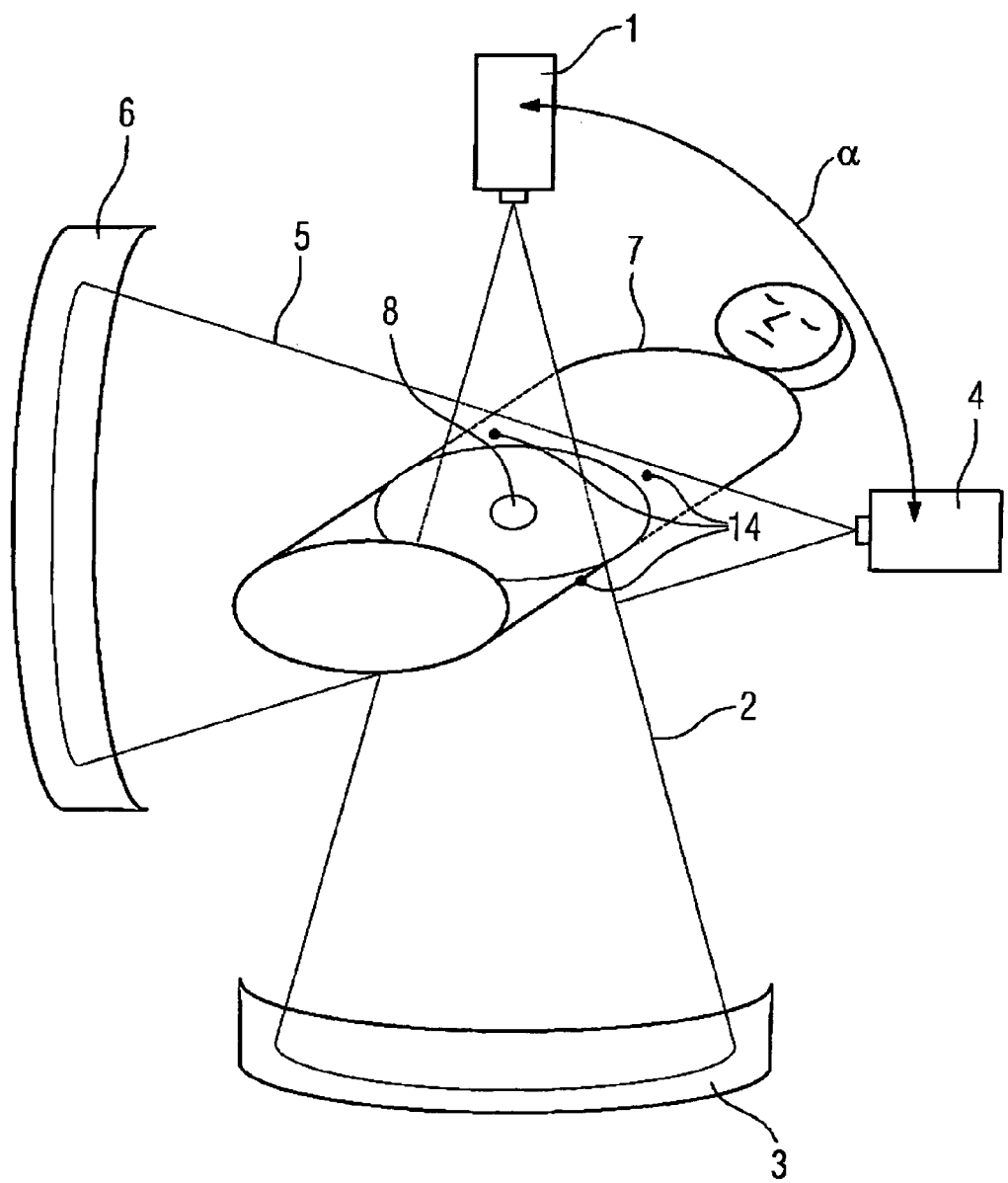
FIG. 6 illustrates an example embodiment with markers applied to the patient.

Furthermore, the position of organs, tumors or other structures in the patient can also be determined indirectly by way of markers which are applied to the patient at predetermined positions and can be identified particularly clearly in the topographic scan. FIG. 6 illustrates an example embodiment in which a position of at least one of an organ and a tumor is determined indirectly via markers 14, which are applied to the patient. In this example, if the relative position and orientation of the markers on the patient are known, then, by way of example, it is possible to deduce the position and orientation of a tumor from the position of the markers 14, which can be identified particularly easily. This indirect position and orientation determination can be used in a particularly helpful manner for the positioning of a patient for radiation therapy.

The position, orientation and extent can now be described in three-dimensional space by simple geometric observations, taking account of the scan geometry. This improved knowledge of the spatial orientation of an organ in the patient can now be used for radiation therapy. In addition, however, it may also be helpful to determine the precise position and/or orientation of the surrounding tissue in the same way, in order to damage this tissue as little as possible when the radiation therapy is calculated.

Radiation therapy relates, of course, to tumorous organs or organ areas, although, instead of determination of a tumor that is limited to one organ, it is also possible to determine the position and orientation of a tumor which extends over a number of organs.

It is self-evident that the features of the invention as stated above can be used not only in the respectively stated combination but also in other combinations or on their own without departing from the scope of the invention.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining of at least one of the position and orientation of three-dimensional structures of a patient, comprising:
    recording one topographic scan of the patient per tube detector combination with the aid of a computed tomography scanner including at least two tube detector combinations arranged at a fixed angle to one another, wherein each detector includes at least one row with a relatively large number of individual detector elements, and wherein the at least two tube detector combinations are moved exclusively linearly parallel to a system axis of the computed tomography scanner and relative to the patient; and
    determining of at least one of the position and orientation of three-dimensional structures of the patient based on the recorded topographic scans; wherein
        only three topographic scans are recorded with only three tube detector combinations simultaneously, wherein the three tube detector combinations are arranged at an angle of 120° to one another.

2. The method as claimed in claim 1 wherein the determining step determines at least one of a position and extent of tumors from simultaneously recorded topographic scans.

3. The method as claimed in claim 2, wherein a position of at least one of an organ and a tumor is determined indirectly via markers which are applied to the patient.

4. The method as claimed in claim 1 wherein the determining step determines at least one of a position and extent of the patient from simultaneously recorded topographic scans.

5. The method as claimed in claim 1, wherein tube detector combinations are used which each have their own detector which covers exclusively one beam fan of a tube.

6. The method as claimed in claim 5, wherein curved detectors are used, and wherein the topographic scans recorded by these detectors are converted to the geometric data of a virtual, planar detector.

7. The method as claimed in claim 1, wherein tube detector combinations are used which include at least two tubes and a single common detector in the form of a circular arc and covering 360°, wherein each tube produces a beam fan which does not overlap the other beam fan or fans of the other tube or tubes.

8. The method as claimed in claim 1 wherein the determining step determines at least one of a position and extent of tumors from simultaneously recorded topographic scans; and the method further comprises:
    using the determination for dosage planning in radiation therapy.

9. The method as claimed in claim 1 wherein the determining step determines at least one of a position and extent of the patient from simultaneously recorded topographic scans; and the method further comprises:
    using the determination for dosage modulation in a CT scan.

10. A method for determination of at least one of the position and orientation of three-dimensional structures of a patient, comprising:
    recording one topographic scan of the patient per tube detector combination with the aid of a computed tomography scanner including at least two tube detector combinations arranged at a fixed angle to one another, wherein each detector includes at least one row with a relatively large number of individual detector elements, and wherein the at least two tube detector combinations are moved exclusively linearly parallel to the system axis of the computed tomography scanner and relative to the patient; and determining of at least one of the position and orientation of three-dimensional structures of the patient based on the recorded topographic scans; wherein the tube detector combinations include at least two tubes and a single common detector in the form of a circular arc and covering 360°, wherein each tube produces a beam fan which does not overlap the other beam fan or fans of the other tube or tubes.

11. The method as claimed in claim 10, wherein only two topographic scans are recorded simultaneously with only two tube detector combinations, wherein the two tube detector combinations are arranged at right angles to one another.

12. The method as claimed in claim 11, wherein the determining step determines at least one of a position and extent of tumors from simultaneously recorded topographic scans; and the method further comprises:

using the determination for dosage planning in radiation therapy.

13. The method as claimed in claim 10 wherein the determining step determines at least one of a position and extent of tumors from simultaneously recorded topographic scans; and the method further comprises:

using the determination for dosage planning in radiation therapy.

14. The method as claimed in claim 10, wherein the determining step determines at least one of a position and extent of tumors from simultaneously recorded topographic scans; and the method further comprises:

using the determination for dosage planning in radiation therapy.

15. The method as claimed in claim 10, wherein the determining step determines at least one of a position and extent of tumors from simultaneously recorded topographic scans.

16. The method as claimed in claim 10, wherein the determining step determines at least one of a position and extent of the patient from simultaneously recorded topographic scans.

17. The method as claimed in claim 10, wherein the determining step determines at least one of a position and extent of the patient from simultaneously recorded topographic scans; and the method further comprises:

using the determination for dosage modulation in a CT scan.

18. A method for determination of at least one of the position and orientation of three-dimensional structures of a patient, comprising:

recording one topographic scan of the patient per tube detector combination with the aid of a computed tomography scanner including at least two tube detector combinations arranged at a fixed angle to one another, wherein each detector includes at least one row with a relatively large number of individual detector elements, and wherein the at least two tube detector combinations are moved exclusively linearly parallel to the system axis of the computed tomography scanner and relative to the patient; and determining of at least one of the position and orientation of three-dimensional structures of the patient based on the recorded topographic scans; wherein a position of at least one of an organ and a tumor is determined indirectly via markers which are applied to the patient.

19. The method as claimed in claim 18, wherein tube detector combinations are used which each have their own detector which covers exclusively one beam fan of a tube.

20. The method as claimed in claim 18, wherein curved detectors are used, and wherein the topographic scans recorded by these detectors are converted to the geometric data of a virtual, planar detector.

21. The method as claimed in claim 20, wherein a position of at least one of an organ and a tumor is determined indirectly via markers which are applied to the patient.

22. The method as claimed in claim 18, wherein tube detector combinations are used which include at least two tubes and a single common detector in the form of a circular arc and covering 360°, wherein each tube produces a beam fan which does not overlap the other beam fan or fans of the other tube or tubes.

23. The method as claimed in claim 18, wherein curved detectors are used, and wherein the topographic scans recorded by these detectors are converted to the geometric data of a virtual, planar detector.

24. The method as claimed in claim 18, wherein only two topographic scans are recorded simultaneously with only two tube detector combinations, wherein the two tube detector combinations are arranged at right angles to one another.

25. The method as claimed in claim 24, wherein tube detector combinations are used which each have their own detector which covers exclusively one beam fan of a tube.

26. The method as claimed in claim 24, wherein tube detector combinations are used which include at least two tubes and a single common detector in the form of a circular arc and covering 360°, wherein each tube produces a beam fan which does not overlap the other beam fan or fans of the other tube or tubes.

27. The method as claimed in claim 24, wherein curved detectors are used, and wherein the topographic scans recorded by these detectors are converted to the geometric data of a virtual, planar detector.

28. The method as claimed in claim 24, wherein the determining step determines at least one of a position and extent of tumors from simultaneously recorded topographic scans; and the method further comprises:

using the determination for dosage planning in radiation therapy.

29. The method of claim 18, wherein only three topographic scans are recorded with only three tube detector combinations simultaneously, wherein the three tube detector combinations are arranged at an angle of 120° to one another.

30. The method as claimed in claim 29, wherein tube detector combinations are used which each have their own detector which covers exclusively one beam fan of a tube.

31. The method as claimed in claim 29, wherein tube detector combinations are used which include at least two tubes and a single common detector in the form of a circular arc and covering 360°, wherein each tube produces a beam fan which does not overlap the other beam fan or fans of the other tube or tubes.

32. The method as claimed in claim 29, wherein curved detectors are used, and wherein the topographic scans recorded by these detectors are converted to the geometric data of a virtual, planar detector.

33. The method as claimed in claim 29, wherein the determining step determines at least one of a position and extent of the patient from simultaneously recorded topographic scans; and the method further comprises:

using the determination for dosage modulation in a CT scan.

* * * * *